Aug. 12, 1941. R. L. BYRUM Plant Pat. 485
ROSE PLANT
Filed April 9, 1941
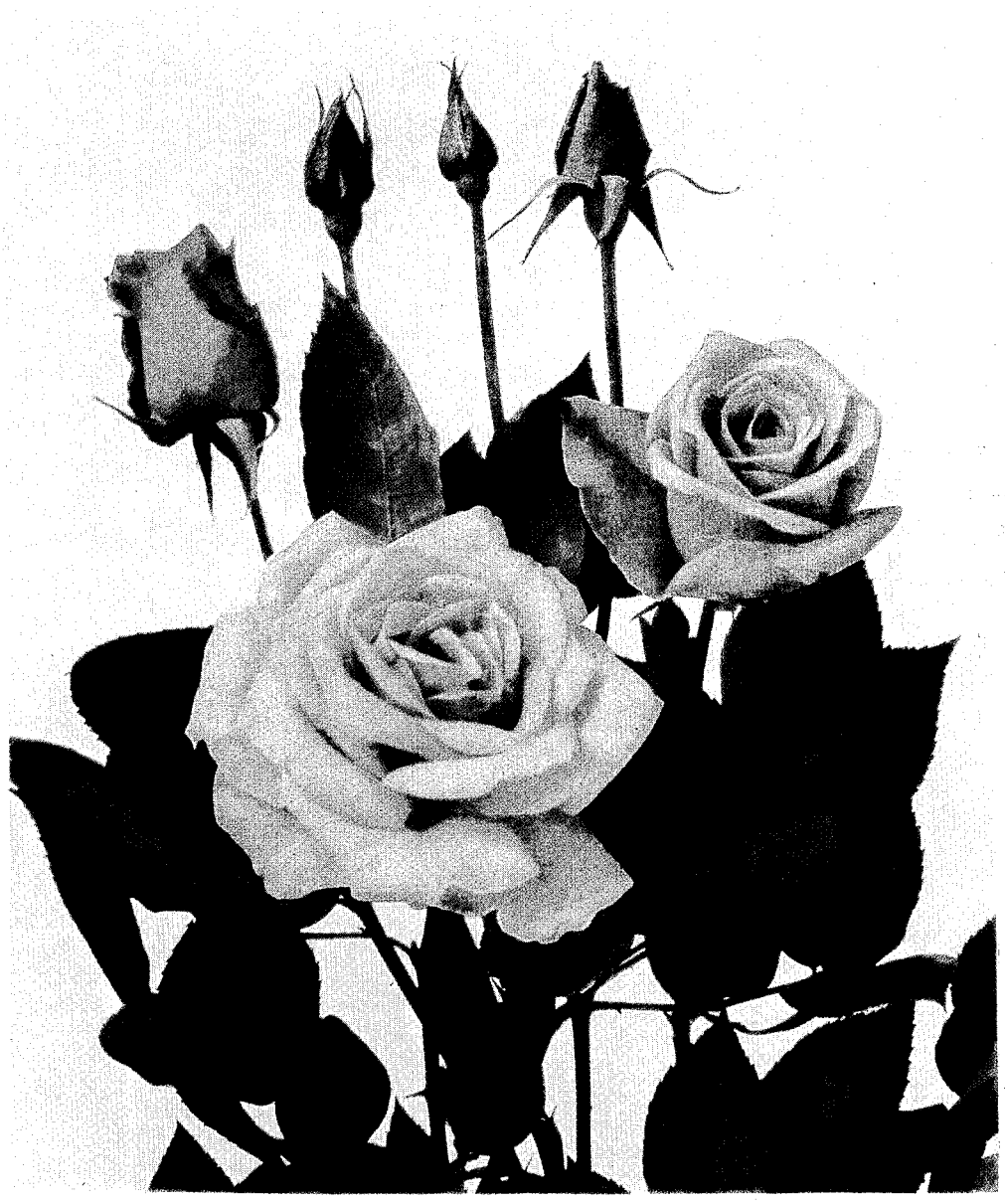
Inventor
R. L. Byrum
By Robbins & Robbins
attorneys Patented Aug. 12, 1941

Plant Pat. 485

UNITED STATES PATENT OFFICE

485

ROSE PLANT

Roy L. Byrum, Richmond, Ind., assignor to Jos. H. Hill Company, Richmond, Ind.

Application April 9, 1941, Serial No. 387,755

1 Claim. (Cl. 47—61)

The present discovery relates to improvements in rose plants of the hybrid tea class, and in particular to a sport found by me on a "Lucile Hill" plant intended to be used in the laboratory for hybridizing purposes.

It was observed that this sport was novel and distinct in a number of respects with regard to the known varieties. The nearest similar variety is its parent "Lucile Hill" and it differs importantly therefrom in that:

(1) It has more petals than "Lucile Hill."

(2) The variety "Lucile Hill" changes from Rose Red to Spinel Pink when half blown, and then remains Spinel Pink both inside and outside. The present sport of this variety, however, on the outside changes from Rose Red and Carmine to Rose color and finishes when fully open as Spinel Pink, while as to the inside it starts out as velvety Carmine and Rose Red, and then changes to all Rose Red and finally finishes when fully open as Rose color.

(3) The foliage is better, being of darker green and more leathery.

The new variety has been asexually reproduced and found to hold its distinguishing characteristics through succeeding propagations by cuttings, grafting, and budding.

The various characteristics of this new rose are set forth in the following detail description, color terminology being in accord with Ridgway's Color Standard.

Type: Bush; greenhouse; sport; for cut flowers.
Class: Hybrid tea.
Parentage: Sport.
*Parent.*—Lucile Hill.

*Flower*

Locality where grown: Richmond, Indiana.
Flowers borne: Singly, on strong, long stems.
Quantity of bloom: Free in greenhouse.
Continuity: Continuous.
Fragrance: Slight tea.
Bud:

*Peduncle.*—Long; heavy; stiff; surface of peduncle away from the sun, Parrot Green, Plate VI, and surface of peduncle on sunny side, Parrot Green, overlaid with Raw Umber and Argus Brown, Plate III; few prickles, Shrimp Pink, Plate I.

*Before calyx breaks.—Size*—large. *Form*—long, pointed with a conspicuous neck; with foliaceous appendages on the surface of the bud; with slender, bristle-like foliaceous parts extending beyond the tip of the bud equal to one-fourth of its length.

*As calyx breaks.—Color*—Rose Red, Plate XII, with longitudinal streaks of Carmine, Plate I.

*As first petal opens.—Size*—large. *Form*—long, pointed. *Color*: outside—mainly Rose Red, with Carmine, Plate I, tip. This observation made in the month of November is modified when made in February, at which latter time the outside is Rose Red with wide, longitudinal streaks of Carmine and Oxblood Red tip (Plate I), inside color remaining unchanged; inside—mainly velvety Carmine with Rose Red near base and spot of Yellow at tip of base. *Opening*—opens up well.

Bloom:

*Size.*—When fully open, very large; six inches average.

*Petalage.*—Double; twenty-five to thirty-five petals, arranged irregularly.

*Form.*—Full, retaining same form at maturity; pedals remaining at first loosely rolled outward; becoming later, at maturity, loosely rolled outward.

Petals: Thick, leathery; with inside and outside satiny.

*Shape.*—Outside—broad obovate with apex flat. Intermediate—obovate with apex flat. Inside—obovate with apex flat, with one notch.

This description of a newly opened flower (when full) made from a rose grown in greenhouse, in November, 1940, at Richmond, Indiana:

*Outside.*—Gradually changes from Rose Red (when half open) to Spinel Pink, as bloom opens to full.

*Inside.*—Gradually changes from velvety Carmine through Rose Red to Rose color, as bloom opens to full.

*Color.*—Outside petal: outside surface—Spinel Pink, Plate XXVI; inside surface—Rose color, Plate XII. Intermediate petal: outside surface—Spinel Pink, Plate XXVI; inside surface—Rose color, Plate XII. Inner petal: outside surface—Spinel Pink, Plate XXVI, with longitudinal streak of White in center. Inside surface—Rose color, Plate XII.

This description was made from a rose that was open for three days in a greenhouse, in November, 1940, at Richmond, Indiana:

*Outside petal.*—Outside surface—Spinel Pink, Plate XXVI. Inside surface—Rose color, Plate XII.

*Inside petal.*—Outside surface—Spinel Pink, Plate XXVI. Inside surface—Rose color, Plate XII.

*General color effect.*—Newly opened flower—Rose color, Plate XII. Three days open—Rose color, Plate XII.

*Behavior.*—Persist.

*Flower longevity.*—Cut roses grown in greenhouse kept at living room temperature, five days in November.

*Reproductive organs*

Stamens: Many; arranged regularly about pistils.
Filaments: Medium length; reddish; most with anthers.
Anthers: Medium size; Brown; all open at once.
Pollen: Moderate; Gold.
Pistils: Medium number.
Styles: Even; short, medium heavy, bunched.
Stigma: White.
Ovaries: All enclosed in calyx.
Sepals: Permanent; short; curled.

*Color.*—Inside base—Pale Yellow-Green, Plate VI, shading to Parrot Green, Plate VI, toward tip. Outside—Grass Green, Plate VI.

Hips: No hips or seeds formed as yet.

*Plant*

Foliage:

*Leaves.*—Compound of five leaflets; very abundant; large; leathery.

*Leaflets.*—*Shape*—oval with apex acute; base round; margin simply irregularly serrate.

*Color.*—*Mature*: upper surface—Dusky Yellowish Green, Plate XLI; under surface—Deep Dull Yellow Green, (1) Plate XXXII. *Young*—the color of the young leaflet does not appear in the Ridgway Chart, and, therefore, it is indicated to be a shade of Green overlaid with Bronze or Red, giving a two-tone effect that varies as the leaflet is moved.

*Rachis.*—The supporting stem of the compound leaf—medium heavy. Upper side—smooth; grooved.

Stipules.—Short; narrow; with short points turning out at an angle of less than 45°.

*Disease.*—Resistant to mildew and blackspot.

Growth:

*Habit.*—Upright; much branched.

*Growth.*—Vigorous.

*Canes.*—Heavy.

*Main stems.*—Dull Green. *Thorns*—several; medium length; hooked downward; with long, narrow base. *Prickles*—none. *Hairs*—none.

*Branches.*—Bright Green. *Thorns*—several; medium length; hooked downward; with long, narrow base. *Prickles*—none. *Hairs*—none.

*New shoots.*—Bronze-Red. *Thorns*—several; medium length; hooked; with short, narrow base. *Prickles*—none. *Hairs*—none.

What I claim is:

A new and distinct variety of hybrid tea rose plant, characterized as to novelty by its distinctive dark and leathery foliage, the predominating rose red color up to the fully opened stage then changing to rose color in the vivid combination coloring of its flowers, the large size of flower and number of petals thereof, substantially as shown and described.

ROY L. BYRUM.